US00PP09984P

United States Patent [19]

Dümmen

[11] Patent Number: Plant 9,984

[45] Date of Patent: Jul. 29, 1997

[54] NEW GUINEA IMPATIENS PLANT NAMED DUEANDO

[75] Inventor: Günter Dümmen, Rheinberg-Eversael, Germany

[73] Assignee: Dümmen Jungpflanzenkulturen, Rheinburg-Eversael, Germany

[21] Appl. No.: 610,295

[22] Filed: Mar. 4, 1996

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 7,789 2/1992 Drewlow ..... Plt./87.6

*Primary Examiner*—James R. Feyrer
*Assistant Examiner*—Melissa L. Kimball
*Attorney, Agent, or Firm*—C. A. Whealy

[57] ABSTRACT

A new and distinct cultivar of New Guinea Impatiens plant named Dueando, characterized by its pure white flowers; compact growth habit; moderate vigor; freely branching plant habit; dark green and glossy non-variegated foliage; early flowering; and weather-tolerant flowers.

1 Drawing Sheet

The present invention relates to a new and distinct cultivar of New Guinea Impatiens plant, botanically known as *Impatiens hawkeri,* known as the variety Dueando. It is anticipated that this plant will be domestically marketed under the synonym "HWD Glissando".

The new cultivar is a product of a planned breeding program conducted by the inventor in Rheinberg, Germany. The objective of the breeding program was to develop a new pure white-flowered variety that had flowers resistant to wind and rain damage or weather-tolerant.

The new cultivar originated from a cross made by the inventor of the proprietary selection 89-002-4 as the male or pollen parent with the New Guinea Impatiens cultivar Jasius (disclosed in U.S. Pat. No. P.P. 7,345) as the female or seed parent.

The cultivar Dueando was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Impatiens are stabilized and reproduced true to type in successive generations of asexual reproduction.

The following traits have been repeatedly observed and are determined to be the unique characteristics of Dueando. These characteristics in combination distinguish Dueando as a new and distinct cultivar:

1. Pure white flowers.
2. Compact growth habit.
3. Moderately vigorous.
4. Freely branching plant habit.
5. Dark green and glossy non-variegated foliage.
6. Early flowering.
7. Flowers that are very weather-tolerant.

In comparison to the parent selection 89-002-4, the new Impatiens is more compact, more freely branching and flowers are more weather-tolerant.

the new Impatiens is most similar to the parent cultivar Jasius. Compared to plants of the cultivar Jasius, plants of the new Impatiens have shorter leaves, flower earlier, have more but smaller flowers, and have flowers that are more weather-tolerant.

The accompanying colored photograph illustraates the overall appearance of the new cultivar, showing the colors as true as it is reasonably possible to obtain in colored reproductions of this type. The photograph comprises a top perspective view of a typical potted plant of Dueando with one plant in a 15-m container.

The cultivar Dueando has not been observed under all possible environmental conditions. The phenotype may vary somewhat with variations in environment such as temperature and light intensity, without, however, any variance in genotype. The following observations, measurements and comparisions describe plants grown in Rheinberg, Germany, under commercial practice in a glass covered greenhouse with day temperatures of 28C, night temperatures of 20 to 22C, and light levels of 30,000 to 40,000 lux. In the following description, color references are made to The Royal Horticultural Society Colour Chart except where general terms of ordinary dictionary significance are used.

Classification:

*Botanical.*—*Impatiens hawkeri.*

*Commercial.*—New Guinea Impatiens.

*Cultivar.*—Dueando.

Parentage:

*Male parent.*—Proprietary selection 89-002-4.

*Female parent.*—New Guinea Impatiens cultivar Jasius (U.S. Pat. No. P.P. 7,345).

Propagation:

*Type cutting.*—Terminal cuttings.

*Time to initiate roots.*—Summer: 27C, 21 days; winter: 20C, 28 days.

Plant description:

*General appearance.*—Rounded; freely branching and compact growth habit; spreading; moderately vigorous; suitable for 10 to 16-cm pots.

*Plant height.*—22 cm from soil level to top of plant plane.

*Foliage description.*—Shape: Elliptic with acuminate tip and attenuate base. Size: Length:8.5 to 10 cm. Width: 2.5 to 3 cm. Texture: Smooth, glossy, and glabrous. Margin: Ciliate. Petiole length: 1 to 1.5 cm. Color: Young foliage, upper surface: Brighter green than 147A. Young foliage, under surface: Greener than 147B. Mature foliage, upper surface: Brighter green than 147A. Mature foliage, under surface: Greener than 147B. Venis, upper surface: Lighter than 144A. Veins, under surface: 144A. Petiole: 144A with overtones of 53B.

*Stem description.*—Internode length: 5 to 8 cm. Stem color: 144A, almost translucent. Just above nodes, small areas of 183B. Vertical lines along stem, 183B.

Flowering description:

*Flowering habit.*—Freely flowering and very early.

*Natural flowering season.*—Year-round. Very early flowering. Under summer conditions, plants flower 5.5 to 6.5 weeks after planting; under winter conditions, plants flower 8 to 10 weeks after planting.

*Flowers borne.*—Flower buds develop in apical leaf axils. Open flowers are displayed above the foliage.

*Quantity of inflorescences.*—Very floriferous; usually 8 to 10 buds and flowers per axil; usually 15 to 20 open flowers per plant open at one time.

*Flower longevity on plant.*—From opening, flowers will last 6 to 9 days.

*Flower diameter.*—5.5 cm.

*Flower depth (height).*—1.5 cm.

*Petals.*—Shape: Cordate. Quantity, arrangement: 5 petals overlapping. Aspect: Flat. Size: Length: 3 cm. Width: 2.8 cm. Texture: Smooth, satiny, and glabrous. Margin: Entire. Color: When opening: 155D. Upper surface: 155D, iridescent. Under surface: 155D. Fading to: Petal color does not fade, maintains pure white color.

*Peduncle.*—Angle: Erect. Length: 4.5 cm. Color: 144A almost translucent.

*Flower bud.*—Shape: Ovoid with spur. Length: 1.7 cm. Diameter: 1 cm. Color: 155B.

*Spur.*—Shape: Needle-shaped, curved at end. Color: Young: 145B. Mature: 145C.

*Sepals.*—Arrangement: Opposite. Quantity: 2. Shape: Ensiform with acuminate tip. Texture: Smooth and glabrous. Margin: Entire. Color: 144A.

*Reproductive organs.*—Androecium: Stamen number: 5. Anther color: Base, 155D; top, 11C. Pollen color: 11D. Gynoecium: Stigma color: Translucent. Ovary color: 144A. Ovary size: 1 to 2 mm. Seed: Seed development is rarely observed.

Disease resistance: No fungal, bacterial nor viral problems observed.

It is claimed:

1. A new and distinct cultivar of New Guinea Impatiens plant named Dueando, as illustrated and described.

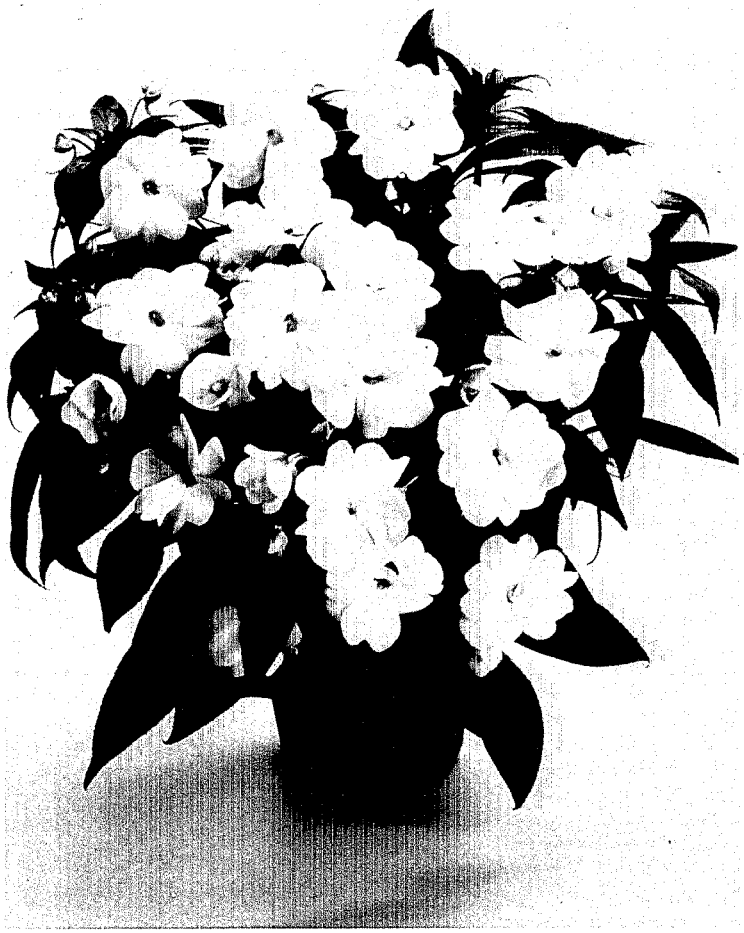

* * * * *